United States Patent [19]

Brink et al.

[11] Patent Number: 4,788,983

[45] Date of Patent: Dec. 6, 1988

[54] PULSE RATE CONTROLLED ENTERTAINMENT DEVICE

[76] Inventors: Loren S. Brink, 3031 Lakeshore Dr., Minneapolis, Minn. 44516; James R. Newton, 5262 Sixth St., NE., Columbia Heights, Minn. 55421

[21] Appl. No.: 932,304

[22] Filed: Nov. 19, 1986

Related U.S. Application Data

[63] Continuation of Ser. No. 760,932, Jul. 31, 1985, abandoned.

[51] Int. Cl.⁴ ............................................. A61B 5/02
[52] U.S. Cl. ................................... 128/734; 128/706; 128/637
[58] Field of Search ............... 128/637, 687, 689, 690, 128/670, 696, 700, 701, 703, 704, 706, 707, 708, 709, 710, 732, 734

[56] References Cited

U.S. PATENT DOCUMENTS

| Re. 28,529 | 8/1975 | Edenhofer | 128/706 X |
|---|---|---|---|
| 3,524,058 | 8/1970 | Robertson | 128/734 X |
| 3,605,727 | 9/1971 | Zenerich | 128/2.06 A |
| 3,978,849 | 9/1976 | Geneen | 128/2.05 T |
| 3,991,747 | 11/1976 | Stanly et al. | 128/2.06 R |
| 4,008,714 | 2/1977 | Silva et al. | 128/734 |
| 4,014,323 | 3/1977 | Gilner et al. | 128/2.12 |
| 4,281,663 | 8/1981 | Pringle | 128/689 |
| 4,312,358 | 1/1982 | Barney | 128/670 |
| 4,367,752 | 1/1983 | Jimenez et al. | 128/689 |

FOREIGN PATENT DOCUMENTS 2135019  1/1972  Fed. Rep. of Germany ...... 128/734

Primary Examiner—Edward M. Coven
Attorney, Agent, or Firm—Orrin M. Haugen; Thomas J. Nikolai

[57] ABSTRACT

A control circuit for a portable radio or like entertainment device which allows it to play only so long as the user's heart rate lies within a range commensurate with safe, effective exercise activity. EKG signals are picked up by suitably placed electrodes, amplified, filtered, shaped and applied in one arrangement to a programmable microprocessor and in another arrangement to a linear circuit phase lock loop and window comparator. In each instance, a determination is made as to whether the user's heart rate is between a lower limit of effective exercise and an upper limit of safe exercise. When the heart rate is outside the limit, the entertainment device is rendered inoperative, thus providing an incentive to tailor the level of exertion so that the heart rate will lie within the desired range.

9 Claims, 3 Drawing Sheets

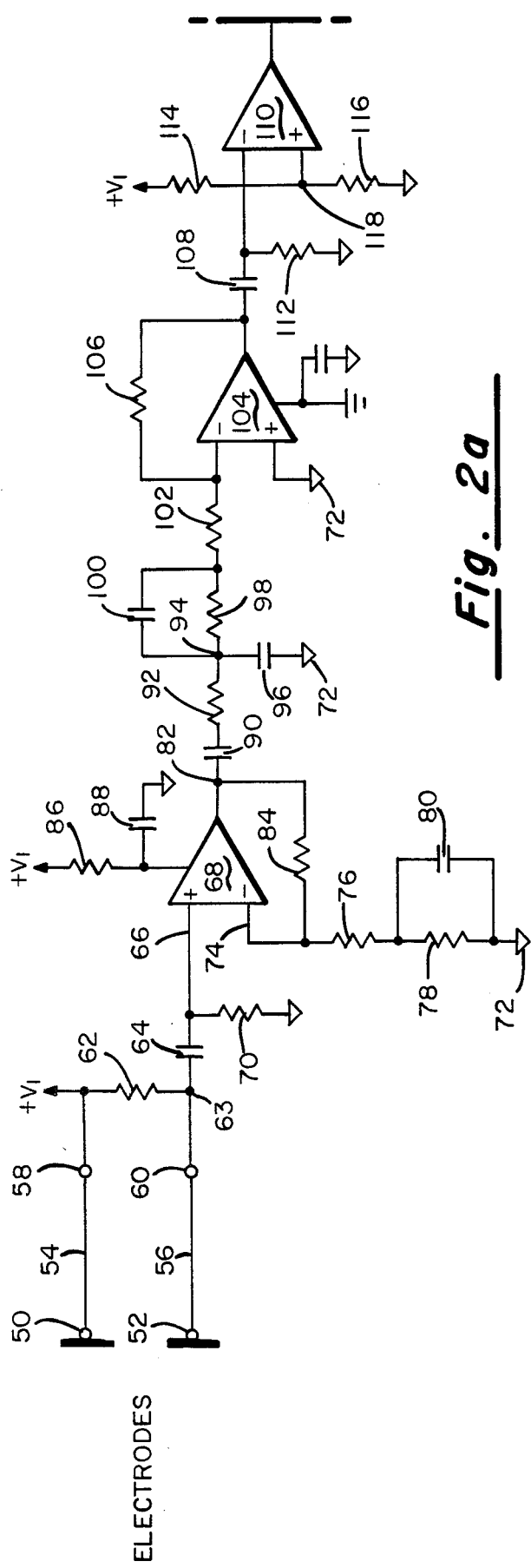

PULSE RATE CONTROLLED ENTERTAINMENT DEVICE

This is a continuation of application Ser. No. 760,932, filed July 31, 1985, now abandoned.

BACKGROUND OF THE INVENTION

I. Field of the Invention

This invention relates generally to pulse rate control of a portable entertainment device, and more particularly to a system for controlling the playing of a radio or an audio or video cassette used during physical exercise so that the device will play only if the person's heart rate lies within a preset frequency band.

II. Discussion of the Prior Art

While undergoing a course of exercise, it has become quite popular for the person involved to listen to music or other audio entertainment through earphones connected to a radio receiver/audio cassette player or while watching a video cassette or broadcast exercise programs on T.V. The music or other programming helps to alleviate the boredom which often accompanies an extended period of physical exercise. Thus, one commonly sees joggers, bikers, aerobic dancers, etc. wearing earphones or watching T.V. while exercising.

It is also well known that for a program of exercise to be effective, it must be sufficiently strenuous to produce a heart rate above some lower threshold but below a preset upper threshold. Between these two thresholds is a so-called "window of exercise". If the exercise produces heart rates below the lower threshold then, it is not particularly useful to the cardiopulmonary system. On the other hand, if the exercise is so strenuous that the heart rate exceeds an upper threshold, then the exercise may be placing too great a strain on the system and could cause negative results. The thresholds, of course, are unique to the particular person undergoing the exercise program and depend, for example, on age, weight, the condition of the cardiovascular system, etc.

A variety of devices are on the market for indicating heart rate during the course of exercise. Certain of these devices also provide an alarm if and when the exercise is resulting in a person's heart rate falling outside of the window. One such device is the ET 2000 which is manufactured and sold by Cardio Systems, Inc. of Eden Prairie, Minn. In the case of the ET 2000, electrodes are placed on the chest and conductive leads exceed from those electrodes to an electronic module worn typically on the wrist. Contained within the electronic module is a microprocessor which is programmed to coact with a suitable LED or LCD readout to provide a digital indication of the heart rate being sensed. The device also includes a keypad whereby the upper and lower limits can be programmed into the device. In addition to the digital readout, it also includes a tone generator for producing an audible signal if and when the upper rate limit is exceeded.

SUMMARY OF THE INVENTION

The present invention is deemed to be an improvement of heart rate monitors such as the ET 2000 described above. Rather than merely providing a visual indication of the heart rate and an alarm signal when a predetermined maximum heart rate is exceeded during an exercise regimen, the device of the present invention can be used to couple the heart rate monitor to an entertainment device such as a portable radio, portable recording cassette player or a video cassette recorder so that the entertainment device is able to play only when the person using the device is performing work at a level which places his heart rate within the desired exercise window. If he or she is exercising so slowly that the minimum threshold is not exceeded or if the exercise is so hard that the upper limit is exceeded, the entertainment device will not play. Thus, the system operates to provide an incentive for the person undergoing exercise to maintain the level of exercise so that the heart rate remains within the desired exercise window. In addition, means are provided for allowing the alarm signal to sound through the speaker mechanism of the entertainment device in the event that the upper safe threshold for exercise is exceeded.

In implementing the system, in accordance with a first embodiment, surface electrodes are positioned on the chest and the EKG signal obtained therefrom is amplified and filtered so as to discriminate against all but the R-wave signals in the PQRST complex. The output from the amplifying and filtering stages is then applied to an AC coupled comparator which then outputs a trigger signal only when that signal exceeds a predetermined amplitude threshold. The output from the comparator is applied to the trigger input of a monostable multivibrator or one-shot circuit such that a square wave of a predetermined amplitude and pulse width is generated for each R-wave trigger. The output from the one-shot is, in turn, connected to an appropriate input of an integrated circuit microprocessor chip which, among other functions, has been programmed to convert the pulse-to-pulse interval to a rate signal measured in beats-per-minute. The microprocessor may also be programmed to provide an appropriate control signal when the rate value computed fails between a lower and an upper threshold. Associated with the entertainment device, e.g. a Sony Walkman receiver, is a switching circuit which is responsive to a control signal from the microprocessor for opening the audio output circuit to which the listening headphones are connected. The switching circuit would be in a normally conducting condition, but when appropriately energized, would open the headphone circuit so that the person engaging in the exercise regimen would no longer hear the broadcasted program.

In accordance with an alternative embodiment, the output from the AC coupled comparator is applied to a phase lock loop circuit rather than to a microprocessor. The phase lock loop, in turn, has its output connected to a window comparator circuit and the output of that window comparator circuit, in turn, is operatively coupled to the interface switching circuit associated with the headphones of the portable entertainment device. Additionally, a tone generator circuit may be incorporated whose output is tied directly to the headphone jack rather than to the switching circuit so that if the heart rate is out-of-limits, a tone rather than the broadcast or prerecorded program is fed to the earphones.

OBJECTS

It is accordingly a principal object of the present invention to provide a new and improved device whereby heart rate can be used to control the operation of an external device.

Another object of the invention is to provide a system in which a person's heart rate can be used to control the operation of an entertainment device such as a portable radio or a portable cassette player.

Yet another object of the invention is to provide an electronic control system for a portable entertainment device which will permit that entertainment device to broadcast sound or video presentations only when a person's heart rate lies within a predetermined range or exercise band.

These and other objects and advantages will become apparent to those skilled in the art from the following detailed description of a preferred embodiment, especially when considered in conjunction with the accompanying drawings in which like numerals in the several views refer to corresponding parts.

DESCRIPTION OF THE DRAWINGS

FIG. 2 shows the arrangement of FIGS. 2(a) and 2(b) in forming a composite schematic diagram;

FIGS. 2(a) and 2(b) when arranged as shown in FIG. 2 comprise an electrical schematic diagram of a first embodiment of the invention.

DESCRIPTION OF THE PREFERRED EMBODIMENT

Figure 1:
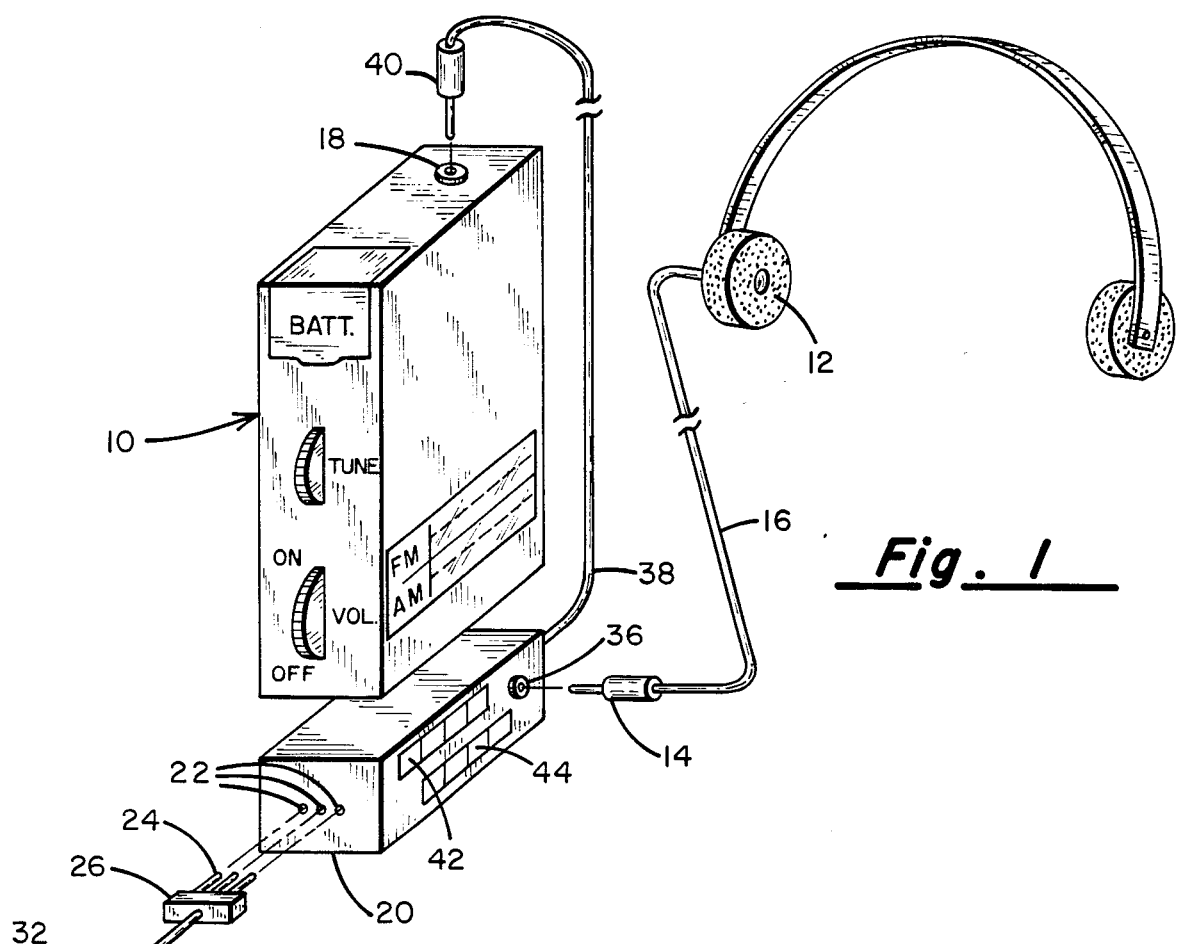
FIG. 1 is a perspective view showing the mechanical features of the present invention.

Referring first to FIG. 1, there is shown a portable entertainment device which is indicated generally by numeral 10 and which may typically be a portable radio capable of receiving both FM and AM broadcast programming. Alternatively, the device 10 may also include a magnetic tape cassette player. Various forms of portable entertainment devices are currently on the market, one popular brand being the so-called Walkman stereo manufactured and sold by the Sony Corporation. The entertainment device of FIG. 1 is shown to include a set of earphones 12 having a male plug 14 and connected thereto by way of an electrical cord 16. The plug 14 is adapted to be inserted into a female jack 18 on the unit 10. The jack 18 is internally coupled to the output circuit of the entertainment device when the device of the present invention is not being used with the device 10.

In carrying out the present invention, there is further provided a module 20 which may be releasably attached to the case of the device 10. The module 20 would include the circuitry indicated schematically in FIGS. 2(a) and 2(b) or 3 hereof, but as far as its mechanical features are concerned, it includes a set of female pin jacks 22 which are adapted to receive prongs 24 on a plug 26 which is electrically coupled to conductors 28 and 30 to skin-contacting electrodes 32 and 34. The electrodes 32 and 34 are of any well-known design and may comprise carbon-impregnated rubber which may be coupled to the skin of the user, preferably on his or her chest surface by adhesive tape patches not shown. Also, a conductive gel may be used to enhance the interfacing of the electrode surfaces 32 and 34 to the wearer's skin.

Extending through the case of the module 20 is a phone jack 36 which is adapted to receive the plug 14 associated with the earphones 12. That is to say, rather than inserting the plug 14 in the jack 18 of the entertainment device 10, the plug 14 is, instead inserted into the jack 36 on the module 20.

Extending out from the module 20 is an electrical cord 38 having a plug-type terminal 40 on the opposite end thereof. When used with the entertainment device 10, the plug 40 is inserted into the normal earphone jack 18 of the entertainment device.

As will be explained in greater detail hereinbelow, contained within the module 20 is circuitry for amplifying and filtering the EKG signals picked up by the skin electrodes 32 and 34 as well as circuitry for developing and displaying pulse rate based upon the average R-R interval. The display becomes observable through the opening 42 in the case of the module 20. Also present on the surface of the module 20 is a suitable input device such as a keypad 44. In use, the keypad may be used to program in an upper rate limit value above which the pulse rate should not be made to progress and a lower rate limit below which not enough physical exercise is taking place to yield any beneficial cardiovascular improvement.

Those skilled in the art will understand that the perspective drawing of FIG. 1 is to be considered as representative only and that the mechanical configuration of the device can be changed significantly without departing from the spirit or scope of the invention. For example, rather than having the module 20 separate from the entertainment device 10, the circuitry comprising the device 20 may be included within the housing of the entertainment device 10. Also, rather than having a keypad 44 as a means of entering the rate limits, thumb wheels, dip switches or other equivalent arrangements can be employed, depending upon the nature of the electrical circuitry contained within the module 20.

Referring next to FIG. 2, there is shown a schematic electrical diagram of a circuit which receives as its input sigals indicative of a physiologic parameter of the human body and which suitably processes such signals to ultimately produce a two-state control signal depending upon whether the rate at which the physiologic signals are produced falls between a first lower threshold level and a second higher threshold level or whether the rate lies outside of the range. The circuit also includes a means for applying the aforesaid electrical control signal to the audio/video entertainment device so that the device can play a program of sound and/or video when the rate being detected is between the lower and upper thresholds.

Referring to FIG. 2(a), then, identified by numerals 50 and 52 are skin-contacting surface electrodes which are coupled by elongated conductors 54 and 56 to input terminals 58 and 60 of the module 20 of FIG. 1. Terminal 58 is coupled through a resistor 62 to a junction point which is tied to the input terminal 60. That junction point 63 is coupled through a coupling capacitor 64 to the non-inverting input 66 of an operation amplifier 68. A biasing resistor 70 is coupled between the input terminal 66 of the operational amplifier and a point of fixed potential such as ground 72. The inverting input 74 of the op amp 68 is connected to the ground 72 by way of series connected resistors 76 and 78. A capacitor 80 is connected in parallel with the resistor 78.

The output terminal of the operational amplifier 68 is identified by numeral 82 and a feedback resistor 84 joins that output terminal to the inverting input 74 of the op amp 68. Operating potentials for the amplifier 68 are obtained from a source of positive potential (+V) via a resistor 86 and a capacitor 88.

The output from the op amp 68 appearing at the output terminal 82 is coupled through a filtered capacitor 90 and a resistor 92 to a junction point 94 between a capacitor 96 and a resistor 98. The other terminal of the capacitor 96 is tied to ground 72 and a further capacitor 100 is connected directly and parallel with the series coupled resistor 98.

A resistor 102 couples the parallel combination of resistor 98 and capacitor 100 to the inverting input of a further operational amplifier 104. The non-inverting input of that amplifier is tied directly to ground 72. A feedback resistor 106 is coupled between the output pin of the operational amplifier 104 and its inverting input terminal.

A coupling capacitor 108 is used to couple the output of the operational amplifier 104 to the inverting input of a still further operational amplifier 110. A resistor 112 is connected between that inverting input of the op amp 110 and ground 72. A voltage divider including series connected resistors 114 and 116 has its common junction 118 tied to the non-inverting input of the operational amplifier 110.

The circuitry thus far described allows a physiologic signal, such as R-waves, in the PQRST complex to be amplified and band pass filtered so that artifacts other than R-waves are suppressed before the resulting signal is applied to the non-inverting input of the operational amplifier 110. The operational amplifier 110 is configured as an AC coupled comparator and, as such, it produces a pulse-type output signal when the input thereto exceeds a predetermined threshold established by the voltage divider consisting of resistors 114 and 116.

The output from comparator 110 appears at a junction pont 120, which is common to one side of a pull-down resistor 122, the input to an integrated circuit phaselock loop 124 and to the input of NOR gate 126. The phaselock loop circuit 124 is preferably a RCA Type 4046 COS/MOS micropower PLL and, as such, consists of a low power, linear voltage-controlled oscillator (VCO) and two different phase comparators having a common signal input amplifier and a common comparator input. The capacitor 128 and the resistors 130 and 132 determine the frequency range of the VCO so that the low-pass filter embodied in the integrated circuit will not be unduly loaded. The source-follower output of the VCO input voltage is provided at terminal 134, i.e., the demodulated output. Resistor 136 is a load resistor for this output and is connected between the terminal 134 and ground. The VCO output is fed to the phaselock loop's comparator by jumper 138 while the comparator output is fed back to the input of the voltage-controlled oscillator by way of the resistor 140.

The output from the phaselock loop appearing at junction point 134 is connected to the non-inverting input of a first operational amplifier 142 and to the inverting input of a second operational amplifier 144. A voltage divider comprising fixed resistors 146 and 148 and a potentiometer 150 is connected in series between a voltage source $+V_1$ and ground, with the wiper arm of the potentiometer being connected to the inverting input of the operational amplifier 142. In a somewhat similar fashion, a voltage divider consisting of fixed resistors 152 and 154 and a potentiometer 156 is connected between the voltage source $+V_1$ and ground and the wiper arm of the potentiometer is connected to the non-inverting input of the operational amplifier 144.

The operational amplifiers 142 and 144 have their output terminals individually coupled to first and second inputs of a NOR gate 158 whose output is coupled through a resistor 160 to the base electrode of a PNP transistor 162. The emitter electrode of this transistor is connected to ground and its collector is coupled through a resistor 164 to one side of a relay coil 166. The other side of the relay coil is coupled to a voltage source $+V_2$. The relay coil 166 controls the normally closed contacts 168 which are connected in series with the stereo headphone jacks 170 and 172.

The output from the operational amplifier 142 is also applied through an inverter 174 to a first input of an oscillator circuit 176 comprising NOR gate 178 and NOR gate 126 with the output from this latter NOR gate being connected by way of a conductor 180 to the second input terminal of the NOR gate 178.

OPERATION OF FIRST EMBODIMENT

Figure 2B:
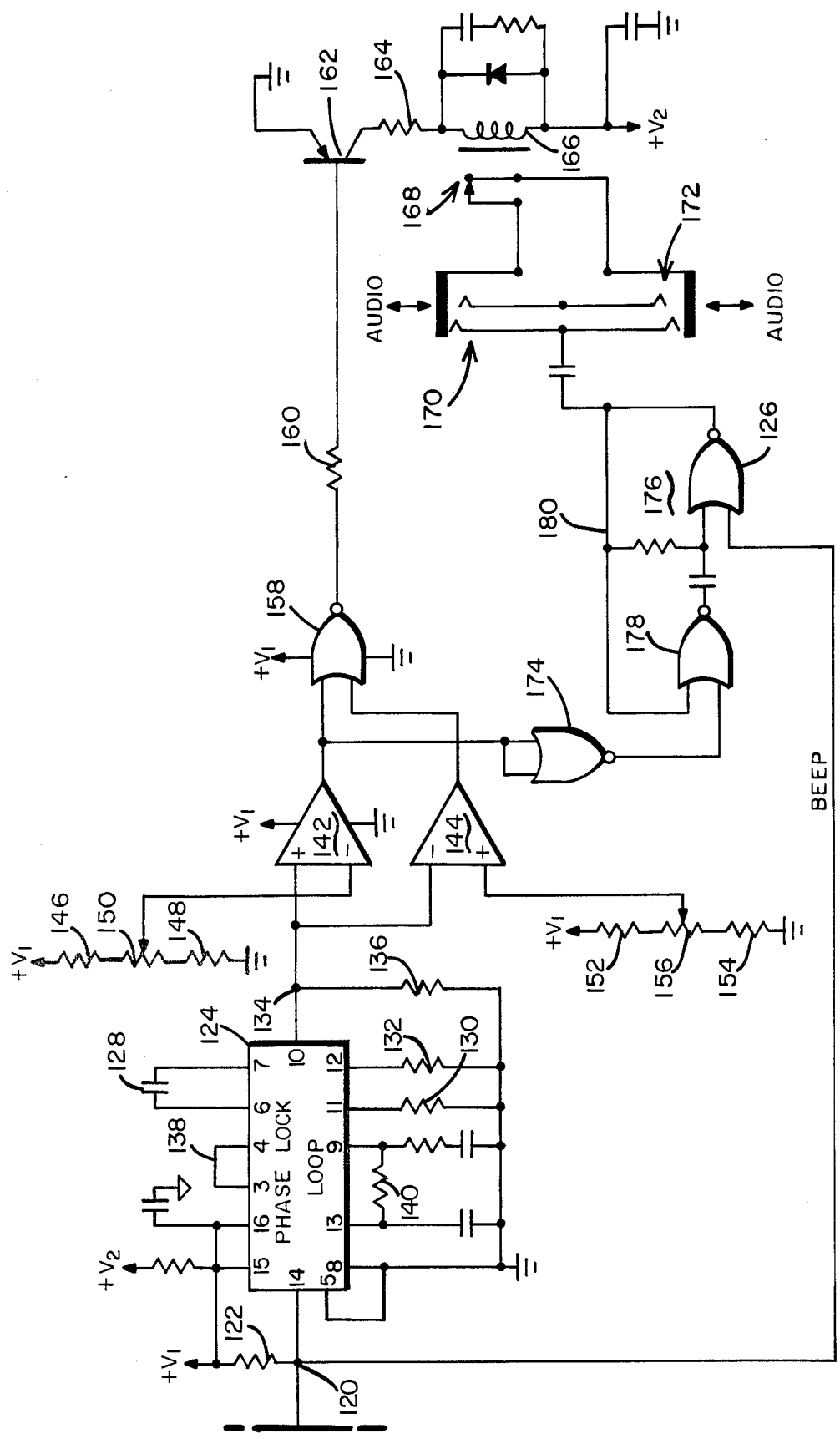

Referring to FIGS. 2(a) and 2(b), the EKG electrodes 50 and 52 are appropriately placed on the user's chestwall using well-known techniques and the resulting voltage signal developed across the high impedance element 62 is fed through the high-pass filter consisting of the series capacitor 64 and the shunt resistor 70 to the non-inverting input of the operational amplifier 68. The op amp 68 is configured to function as an AC coupled non-inverting amplifier whose voltage gain is determined by the ratio of the resistor 84 to the combined series resistance of resistors 76 and 78.

The amplified output from the operational amplifier 68 is fed through a low-pass filter comprising the resistors 92 and 98 and the capacitors 96 and 100. The component values are selected such that high-frequency artifacts are attenuated. From there, the signal is applied to a high-pass filter stage consisting of the operational amplifier 104, the series capacitor 108 and the shunt resistor 112. In this instance, the component values are selected so that the pulse signals picked up by the EKG electrodes pass but lower frequency signals are suppressed.

The resulting waveform is applied to the AC comparator stage consisting of the operational amplifier 110. The threshold for the comparator is set by the voltage divider consisting of resistors 114 and 126 whose common node is connected to the non-inverting input of the comparator 110. Thus, by appropriately choosing the resistance values of the components 114 and 116, the comparator may be made to produce an output only when the signal supplied to its inverting input exceeds the established threshold. In this manner, only electrical artifacts associated with the heart's R-wave cause regularly-shaped pulses to be developed at the comparator output terminal 120.

The phaselock loop 124 operates in a conventional fashion to produce at the demodulator output terminal 134 thereof a voltage signal whose amplitude is proportional to the frequency at which pulses are occurring at the junction point 120. Thus, for low heart beat rates, the effective DC voltage appearing at output terminal 134 tends to be low, but when the heart rate is high, so, too, is the DC voltage appearing at the junction 134.

The voltage proportional to heart rate is then applied to the window comparators 142 and 144. The comparator 142 is configured such that the output therefrom will be a binary low signal so long as it does not exceed the threshold established by the Hi Limit potentiometer 150. Similarly, the output from the window comparator 144 will be low so long as the voltage proportional to heart rate does not fall below a threshold established by the Lo Limit potentiometer 156. So long as both window comparators 142 and 144 are outputting binary low signals, NOR gate 158 will be outputting a high signal, holding the transistor 162 in its relatively non-conducting condition. If, on the other hand, the voltage proportional to heart rate appearing on terminal 134 exceeds the upper threshold established by potentiometer 150 or falls below the threshold established by the potentiometer 156, one or the other of the comparators 142 or 144 will go high, causing NOR gate 158 to output a low signal sufficient to turn on the transistor switch 162. With switch 162 conducting, sufficient current can flow through the relay coil 166 to actuate the contacts 168 to open the headphone circuit so that the music or other programming will not be heard.

When the user's heart rate exceeds the upper limit, the output from window comparator 142 is high which, when inverted by inverter 174, is used to enable the oscillator comprised of NOR gates 178 and 126 to generate an audio tone. The pulses corresponding to heart beats appearing at the junction 120 and applied to the NOR gate 126 causes the tone to be intermittent in nature so that a "beeping" sound is produced in the earphones.

While the settings for the potentiometers 150 and 156 would vary with the particular individual, the circuit may be designed so that the lower limit may be a heart rate value between 30 and 130 beats-per-minute while the upper limit may be set between 85 and 205 beats-per-minute.

ALTERNATIVE EMBODIMENT

Figure 3:
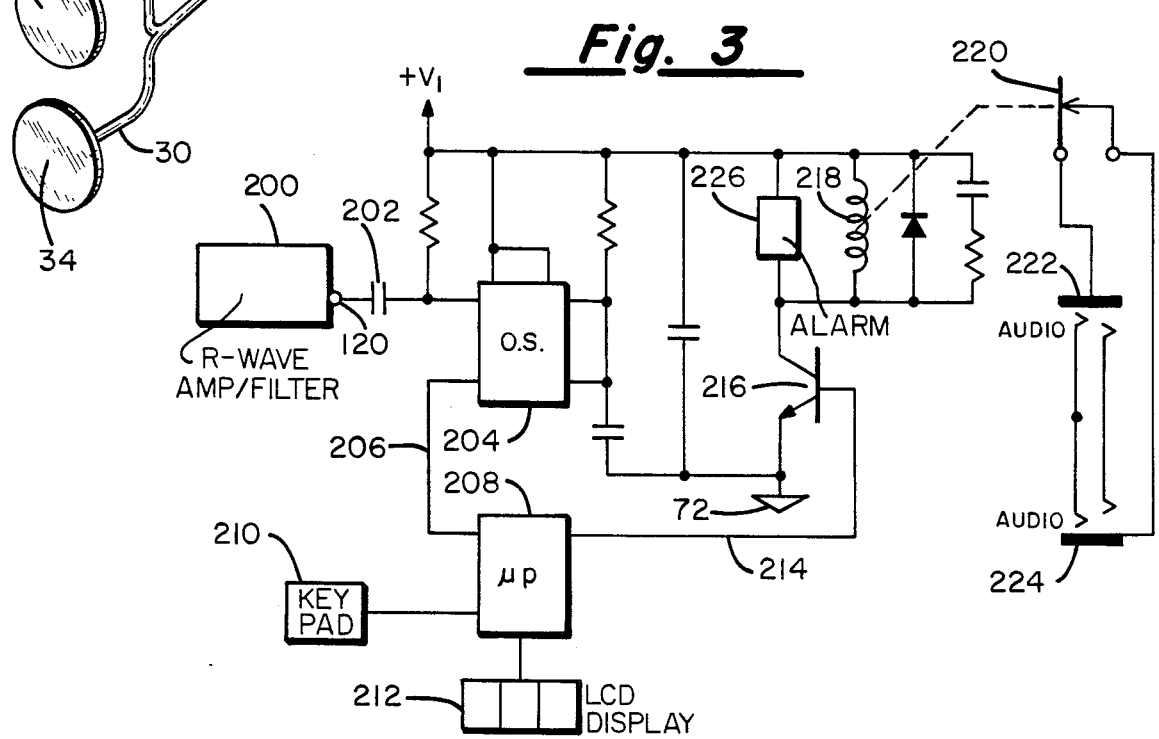
FIG. 3 is an electrical schematic diagram of an alternative embodiment of the present invention.

Referring to FIG. 3, there is shown another way of implementing the system of the present invention. The circuitry contained within the box 200 may be identical to that shown in FIGS. 2(a) and 2(b) to the left of the junction point 120. It will be recalled that the signal appearing at the junction 120 is a well-shaped pulse pattern corresponding to the R-wave activity of the heart. Rather than being applied to a phaselock loop of FIG. 2, the heart rate signals in FIG. 3 are applied via capacitor 202 to the trigger input of a monostable multivibrator or one-shot 204. The one-shot circuit acts a pulse shaper for making the pulse output signals on line 206 compatible with the input specifications for a microprocessor 208.

The microprocessor may be any one of a number of commercially available devices which includes as a part of a single chip the necessary memory for storing a program of instructions and the processing circuitry for executing those instructions. Data signals representing operands to be manipulated may be entered via a keypad 210, again in a known fashion. Thus, as in the case of the ET 2000, the microprocessor may be programmed to convert the R-wave interval to a pulse rate in terms of beats-per-minute, which pulse rate may be displayed on a suitable LCD readout device 212. The keypad 210 can be used for, among other things, entering in an upper rate limit and a lower rate limit to define the window in which safe and effective exercising may cause the heart rate to lie.

So long as the heart rate lies within the prescribed window, the signal on conductor 214 is low such that the NPN transistor 216 is non-conducting. When this transistor is non-conducting, insufficient current flows from the positive source $+V_1$ through the relay coil 218 and the collector to emitter path of the transistor 216 to break the normally closed contacts 220. Hence, the circuit through the audio jacks 222/224 remains intact. However, should the microprocessor detect that the pulses arriving from the one-shot 204 are at too low a rate or too high a rate to fall within the pre-established window of safe, effective exercise, then a positive signal will be produced on line 214 from the microprocessor to turn on the transistor switch 216. Once the switch is rendered conductive, a substantial current flows through the relay coil 218 to open the normally closed contacts 220. With these contacts opened, the audio messages from the portable entertainment device (FIG. 1) are blocked from reaching the earphones. At the same time, a current flows through the alarm device 226 to apprise the user that the window limit has been exceeded.

While the invention has been described herein in considerable detail, in order to comply with the Patent Statutes and to provide those skilled in the art with information needed to apply the novel principles and to construct and use such specialized components as are required, it is to be understood that the invention can be carried out by specifically different equipment and devices, and that various modifications, both as to equipment details and operating procedures can be effected without departing from the scope of the invention itself.

What is claimed is:

1. Apparatus for controlling the on/off state of a portable audio entertainment device carried by a person during the course of an exercise program, in response to achieving a predetermined level of physical activity, comprising:
   (a) means for sensing a physiologic parameter of a human body which changes with level of physical exercise;
   (b) signal processing means coupled to said sensing means for producing an electrical control signal when said physiologic parameter being sensed falls above a first threshold value corresponding to a level of exercise beneficial to the body and below a second threshold value greater than said first value where exceeding said second threshold can be injurious; and
   (c) circuit means for applying said electrical control signal to said portable entertainment device such that said device plays an audio program only when said physiologic parameter falls between said first threshold value and said second threshold value whereby said person is rewarded by the playing of said portable audio entertainment device so long as said person's level of exercise is both safe and effective.

2. Apparatus as in claim 1 wherein said means for sensing a physiologic parameter includes means for detecting pulse rate.

3. Apparatus as in claim 1 wherein said means for sensing a physiological parameter comprises body contacting electrodes and wherein said signal processing means comprising amplifying means coupled to said electrodes and signal filtering means connected to the output of said amplifying means for discriminating against electrical artifacts other than R-waves picked up by said electrodes.

4. Apparatus as in claim 3 and further including a comparator circuit coupled to receive the output from said filtering means for producing a first signal when said output from said filtering means exceds a predetermined voltage level.

5. Apparatus as in claim 4 and further including signal converting means for producing an output signal indicative of the rate at which said first signals are produced.

6. Apparatus as in claim 5 and further including means for producing a binary signal of a first level when said output signal indicative of rate is within a predetermined rate range and a second level when said output signal indicative of rate is outside of said predetermined rate range.

7. Apparatus as in claim 1 wherein the circuit means includes an electrically operated switch having a normally closed state and an open state, said switch being disposed in controlling relation to said on/off state of said entertainment equipment.

8. Apparatus as in claim 7 wherein said entertainment equipment includes listening headphones and said switch is in series circuit with said headphones.

9. Apparatus as in claim 1 wherein said signal processing means and said means for applying said electrical control signal to said entertainment equipment is contained in a housing attachable to said entertainment equipment.

* * * * *